United States Patent
Josic et al.

(10) Patent No.: US 6,893,856 B2
(45) Date of Patent: May 17, 2005

(54) PROCESS FOR PREPARING VIRUS-INACTIVATED FACTORS IX AND X BY MEMBRANE CHROMATOGRAPHY

(75) Inventors: Djuro Josic, Vienna (AT); Ales Strancar, Ajdovsina (SI)

(73) Assignee: Octapharma AG, Lachen (CH)

(*) Notice: Subject to any disclaimer, the term of this patent is extended or adjusted under 35 U.S.C. 154(b) by 11 days.

(21) Appl. No.: 10/136,468

(22) Filed: May 2, 2002

(65) Prior Publication Data

US 2002/0182582 A1 Dec. 5, 2002

Related U.S. Application Data

(63) Continuation of application No. 08/646,331, filed as application No. PCT/EP94/04067 on Jul. 12, 1994, now abandoned.

(30) Foreign Application Priority Data

Dec. 10, 1993 (DE) ........................................ P 43 42 132

(51) Int. Cl.$^7$ ............................ C12N 9/64; C12N 7/06; C02F 1/28
(52) U.S. Cl. ........................ 435/226; 435/238; 210/656
(58) Field of Search ................................ 435/238, 381, 435/384, 226; 210/656

(56) References Cited

U.S. PATENT DOCUMENTS

| | | | | |
|---|---|---|---|---|
| 4,820,805 A | * | 4/1989 | Neurath et al. | 530/410 |
| 5,281,661 A | * | 1/1994 | Linnau et al. | 525/54.1 |
| 5,492,821 A | * | 2/1996 | Callstrom et al. | 435/188 |

FOREIGN PATENT DOCUMENTS

| | | |
|---|---|---|
| DE | 3914869 | 8/1990 |
| EP | 0050061 | 4/1982 |
| EP | 0053338 | 6/1982 |
| EP | 0131740 | 1/1985 |
| EP | 0229026 | 7/1987 |
| EP | 0317376 | 5/1989 |
| EP | 0496725 A2 | 7/1992 |
| EP | 0519901 | 12/1992 |
| WO | 90/05018 | 5/1990 |
| WO | 9315105 * | 8/1993 |

OTHER PUBLICATIONS

Journal of Chromatography, vol. 632, Feb. 19, 1993, Amsterdam NL, pp. 1–10, Josic D. et al.

Journal of Chromatography, vol. 590, 1992, Amsterdam NL, pp. 59–76, Josic D. et al.

* cited by examiner

Primary Examiner—Sandra E. Saucier
(74) Attorney, Agent, or Firm—Jacobson Holman PLLC

(57) ABSTRACT

Disclosed is a process for preparing agents containing virus-inactivated vitamin K-dependent plasma components as well as protein C, protein S, factors II, VII, IX and/or X as well as combinations thereof, such as, for example, PPSB preparations, wherein a source containing these components is subjected to a appropriate separation procedures, especially by using membrane-chromatographic methods.

17 Claims, No Drawings

PROCESS FOR PREPARING VIRUS-INACTIVATED FACTORS IX AND X BY MEMBRANE CHROMATOGRAPHY

This is a continuation of application Ser. No. 08/646,331 filed Aug. 29, 1996, now abandoned, which in turn is a 371 of PCT/EP 94/04067 field Jul. 12, 1994.

The subject matter of the present invention is a process for preparing agents containing virus-inactivated vitamin K-dependent plasma components as well as protein C and protein S from a source containing these components.

Vitamin K-dependent plasma components such as protein C, protein S, the factors II, VII, IX and X are constituents which are contained in blood plasma and play an important role in the pathophysiology of the blood clotting cascade. These factors are employed as medicaments in the therapy of patients exhibiting symptoms caused by a respective deficiency in these factors.

Now, blood plasma is not available in any desired amount as a source for a commercial recovery of the factors. Thus, for both ethical and economic reasons it must be the goal of any fractionation and isolation of these vitamin K-dependent plasma components as well as protein C and protein S to ensure a yield as high as possible of each factor alone by itself, on the one hand, and at the same time to also allow an isolation of each of the other factors, on the other hand. It is the object of the invention to provide a process capable of reaching said goal.

The object as posed is attained by the process according to the invention comprising the features set forth in claim 1

In the process according to the invention, the use of membrane chromatography plays an important role. Josić et al., in Journal of Chromatography, 632 (1993), 1–10, describe the suitability of the heparin affinity chromatography for isolating plasma proteins from the blood clotting cascade. The isolation of antithrombin III and the separation of factor IX and factor X after a preliminary separation by anion chromatography is described. The anion exchanger chromatography for a preliminary separation of factor IX and factor X is effected by preparative HPLC. The enrichment of samples containing factor IX and factor X is accomplished in accordance with H. G. J. Brummelhuis, in J. M. Curling (Editor), "Methods of Plasma Protein Fractionation", Academic Press, London, Orlando, 1980, p. 117.

The high performance membrane chromatography of serum and plasma membrane proteins has already been known from Josić et al., Journal of Chromatography, 590 (1992), 59–76. The separation of serum and plasma membrane proteins has been described therein. For example, plasma membrane proteins from liver and kidney tissues were separated.

Surprisingly it has been shown that valuable vitamin K-dependent plasma ingredients such as protein C, protein S, factors II, VII, IX and X can be obtained in high purity and yield by means of the process described hereinbelow.

In a first step, the sources containing the respective vitamin K-dependent plasma components as well as protein C and protein S, which sources are preferably employed from blood plasma in the fresh or thawed condition, are subjected to a solid phase extraction on anion exchanger materials. The anion exchanger material may be employed as a particulate material in a loose bulk, arranged in membranes or in the form of compact disks. The solid phase extraction on polysaccharides which have been modified with basic groups and optionally cross-linked is preferred. More specifically, materials such as polysaccharides modified with diethylaminoethyl groups (DEAE) or quaternary amines can be used. Thus, e.g., materials such as Sephadex® P 50 may be employed. DEAE-modified separating materials, more particularly, are used for the separation of factor IX. In the solid phase extraction, the source to be extracted is admixed with the material which is present in the solid state.

The solid phase extraction is preferably carried out under conditions of low ionic strength. After steps of washing which are optionally carried out, the effluent is collected and may then be subjected to other work-up steps.

Thus, in order to separate factor IX, the sample is preferably filtered through an appropriately modified membrane. Then the filtrate may optionally be further used, e.g., for the production of albumin.

The proteins bound to the membrane or the respective solid phase material, i.e. factor II, especially factor IX and factor X, are subsequently eluted under conditions of a higher ionic strength from the solid phase. When DEAE- or quaternary amine-modified membranes are used, the multiple usability thereof constitutes an advantage over the solid phase extraction by means of the above-mentioned solid phase extraction materials, especially the particulate materials.

The material adsorbed on the solid phase is then desorbed from the carrier material by the action of solutions having a higher ionic strength. Then the ionic strength of the fraction will be adapted to the conditions required for performing the subsequent separation steps by suitable measures such as dilution or ultrafiltration or diafiltration or addition of agents increasing the ionic strength.

This may be followed by an anion exchanger membrane chromatography or affinity membrane chromatography using immobilized substances having a high or low molecular weight which have a high affinity to the vitamin K-dependent plasma components to be isolated as well as protein C and protein S.

This step of a chromatographic purification may also be effected on materials for carrying out a hydrophobic interaction chromatography.

As the anion exchanger materials, more particularly, membranes modified with diethylaminoethyl groups or quaternary amines, respectively, are to be taken into consideration also here. Substances having a high affinity to the vitamin K-dependent plasma components as well as protein C and protein S may be immunoaffinity ligands. Immunoaffinity ligands to be considered are antibodies directed against the factors to be isolated. Thus, for example, for the isolation of factor IX, membranes carrying respective immobilized antibodies against factor IX can be used. The substances that are not retained by the anion exchanger membrane or immunoaffinity membrane are washed out, optionally collected and further processed.

Typical ligands for the hydrophobic chromatography exhibit some gradual changes in hydrophobicity. They include, for example, acyclic or alicyclic aliphatic compounds having, for example, $C_1$- to $C_{18}$-alkyl chains or aromatic compounds which may also have been modified with polar protic or polar aprotic ligands such as cyano groups. As the hydrophobic ligands suitable for hydrophobic interaction chromatography there are to be especially considered propyl, butyl, phenyl groups by means of which the carrier material has been modified and similar ligands exhibiting some gradual change in hydrophobicity. The gradual change in hydrophobicity may also be effected by polar groups. Thus, more particularly, 2-hydroxyaminoalkyl groups, such as 2-hydroxyaminopropyl groups, are suitable as hydrophobic ligands for the isolation of factor IX.

The next step comprises a further fractionation of the adsorbed plasma components by stepwise elution upon a change in the ionic strength and/or the pH value either with solvent systems of higher ionic strength solvent systems having different polarities or solvent systems reversing the affinity between the immunoaffinity ligand and the substrate. The procedures mentioned above may then be adopted to adjust the ionic strength of the fraction eluting from the membrane to the conditions of further purification.

The optional step f) of claim 1 comprises an affinity membrane chromatography. The affinity membrane chromatography within the scope of the process according to the invention is understood to also include hydrophobic chromatography. Appropriate ligands have already been characterized hereinabove.

The affinity membrane chromatography within the scope of the process according to the invention also relates to chromatographic procedures wherein membranes modified with immunoaffinity ligands are used. Herein, more specifically, monoclonal antibodies against the vitamin K-dependent plasma components as well as protein C and protein S are used, which monoclonal antibodies have been immobilized on the membrane.

The operations of the chromatographic separation of the vitamin K-dependent plasma components as well as protein C and protein S in the sample may be carried out with a use of substrate materials modified with ion exchanger groups, especially anion exchangers, on the one hand, or with a use of materials modified with immunoaffinity ligands, on the other hand.

In a very advantageous mode said chromatographic materials are arranged in membranes. Preferably, the membranes consist of a substrate material such as a modified cellulose or a synthetic fiber. More specifically, membranes as well as compact disks made of porous polyglycidyl methacrylates and/or of ether porous hydrophilic polymers having a similar structure, such as a hydrophilized polystyrene, are suitable.

A membrane suitable for the separation consists of a stack thin porous films made of cellulose of synthetic fibers in the first case, while it consists of compact disks made from silicagel or polymer carriers in the second case. The substrate materials of said membranes of disks have been provided with the appropriate anion exchanger groups or immunoaffinity ligands. The ion exchanger groups, more particularly, may be anion exchanger groups such as quaternary ammonium compounds or diethylaminoethyl (DEAE) groups. The cation exchangers, basically, may be weakly or strongly acidic cation exchangers such as materials modified with sulfonic acid or phosphoric acid groups.

The ion exchanger groups may or may not have been bonded to the fiber of the substrate material through a so-called spacer. Materials provided with spacers are also called tentacle materials. Suitable spacers and ligands have been specified in DE 42 04 694. A glucsoamine moiety, for example, may also serve as a spacer. Anion exchanger groups such as DEAE or quaternary ammonium compounds may also have been bonded to the membranes made of porous polyglycidyl methacrylate or the other materials mentioned. The anion exchanger groups are bonded either directly to the material forming the membrane or also through a spacer, e.g. a glucsoamine moiety.

In another embodiment of the process according to the invention, an affinity membrane chromatography is used which utilizes immobilized low or high molecular weight substances having a high affinity to the vitamin K-dependent plasma components as well as protein C and protein S, which preferably are of human or murine origin.

The substances possessing affinity to the vitamin K-dependent plasma components, factors II, VII, IX or X as well as protein C and protein S are immobilized on the carrier by means of chemically active groups. It is preferred that the active group will not directly attack the carrier material, but will attack at the end of a spacer. The immobilization of the substances having affinity to the factors is effected by bonding same to active grops such as tosyl, tresyl, hydrazide and others. Appropriate procedures have been known from T. M. Phillips, "Affinity Chromatography", in "Chromatography" (E. Heftmann, Ed.), 5th edition, Elsevier, Amsterdam 1992.

The antibodies may also be preliminarily adsorbed on membranes bearing protein A or protein G ligands. The elution of the antibodies (bleeding of the column) may be prevented by a subsequent covalent cross-linking of the column. For cross-linking the antibodies to protein A or protein G membranes, a process similar to that using loose carriers may be employed. The advantage of immobilizing on protein A or protein C consists of that the antibodies are exclusively immobilized on the constant segment of the molecule ($F_c$). Hence, the antigen-binding portion ($F_{ab}$) remains free and is not inhibited in its interaction with the respective factors.

The virus inactivation is effected by treating the fraction obtained after a chromatographic purification with detergents such as ionic and/or non-ionic surfactants, e.g. in the presence of di- or tri-alkylated phosphate compounds, such as, e.g., trin-butyl phosphate according to the method described in EP 0 131 740 A1. Basically, the virus-inactivation may also be carried out prior to first chromatographic step. It is preferred that Triton® X-100 Tween/TNBP (tri-n-butyl phosphate) are used for the virus-inactivation Good results are also obtained with sodium cholate/TNBP. Preferably, quantities of up to 15% by weight of the detergent are used.

However, the virus-inactivation may also be effected by means of a heat treatment. In this procedure, after a first membrane chromatography, the vitamin K-dependent plasma components as well as protein C and protein S are subjected to a step of pasteurization. An appropriate process is proposed in the German patent application P 43 18 435.9. Therein, fractions enriched with factor VIII are brought into contact with di- or trialkyl phosphates and optionally wetting agents in the presence of stabilizers such as sugars, amino acids, bivalent cations and/or heparin and, at the same time or subsequently, are treated at some elevated temperature within the range of from 55° C. to 70° C. for a period of from 5 hours to 30 hours. If so desired, a filtration for removing viruses may also be carried out.

It may be advantageous to combine the two methods of virus-inactivation, treatment with detergents and heat as well as filtration.

In the isolation of factor IX, the pasteurization step is preferably carried out subsequently to step f) of claim 1. This may be followed by another membrane chromatography for removing the chemicals used in said step. It is preferred that the stabilizers added are removed by means of membrane modified with DEAE or quaternary ammonium compounds positioned on the surface of the chromatographic carrier material through a spacer. It is also possible to position the corresponding ligands on the surface of the chromatographic carrier material without using a spacer.

Under the conditions chosen, the stabilizers are not retarded by this anion exchanger material, whereas the factors are adsorbed on the chromatography material.

The stabilizers which in general consist of lower molecular weight substances may also be removed by ultra- or diafiltration. The resulting fractions accumulated with vitamin K dependent plasma components such as protein C and protein S are then concentrated, if so desired. The concentration methods offering themselves are procedures involving the removal of the solvent, usually water, under mild conditions. They include, more specifically, procedures wherein the solvent is removed under reduced pressure, such as, for example, lyophilization (freeze drying) or spray drying.

The utilization of membrane chromatograpy in the process according to the invention, more particularly, implies the advantage of that the chromatographic separation may be carried out considerably faster. Furthermore, the membranes to be utilized can be re-used a multiplicity of times. In contrast thereto, if the solid phase material according to prior art is used, this material cannot be re-used, but will already have to be disposed of if used once.

The process according to the invention is illustrated in greater detail by way of the isolation of factor IX.

EXAMPLE 1

Thawed blood plasma is subjected to a solid phase extraction with Sephadex® P 50. After the elution of the substance adsorbed on the solid phase, the resulting fraction is adjusted to have an ionic strength corresponding to from 10 to 20 mM of sodium citrate at pH 7.4 and is subjected to a membrane chromatography in a DEAE QuickDisk (diameter of 25 mm; thickness of 3 mm). The pressure is approximately 3 bar. Then, chromatography is carried out at a flow rate of 5 ml/min. The pooled fraction contains a mixture of factor II and factor VII and may be subjected to a further work-up. The peak eluting then from the column contains a mixture of factor IX and factor X. Membrane chromatography is carried out by employing a gradient which changes from said initial buffer solution towards a buffer solution comprising 1 M of NaCl as well as from 10 to 20 mM of sodium citrate of pH 7.4 as buffer B. If a strong anion exchanger having a high surface occupation of ligands will be used, a higher capacity will be achieved. Some limiting factor is constituted by the selectivity of the material. The course of the elution gradient will depend on the degree of surface occupation of ligands on the carrier.

The mixture comprising factor IX and factor X is then subjected to further chromatography. The load capacity of the membrane chromatographic material employed is equal to or greater than that of the material in the form of particles, both based on the amount of material.

EXAMPLE 2

The fraction recovered according to Example 1 and containing factor IX/X is treated as per Journal of Chromatography, 632 (1993), 1–10. The fraction containing factor IX/X as obtained according to Example 1 is subjected to a heparin affinity membrane chromatography on a compact disk. After application from a buffer having a relatively low ionic strength, the material is rinsed with a buffer having a ionic strength of about 500 mOsm. Then, factor IX is eluted by using a gradient which starts at about 500 mOsm and increases up to about 1,000 mOsm. The factor IX eluted thereby has a high purity. The rate of the recovery of factor IX, starting from the first work-up step, is about 87%.

What is claimed is:

1. A process for preparing a virus-inactivated plasma component, wherein the component is factor IX, factor X, or a mixture of factors IX and X, comprising the steps of:
    a) applying a source of the plasma component to a solid phase for extraction, the solid phase having anion exchanger materials immobilized thereon, under conditions effecting extraction by adsorption of the plasma component on the solid phase;
    b) applying a desorbing solution to the solid phase, the solution having an ionic strength that effects elution of the plasma component from the solid phase in a resulting eluate comprising the plasma component in the desorbing solution; followed by;
    c) isolation and purification of the plasma component by
        i) applying eluate from the solid phase to a chromatography membrane having immobilized thereon anion exchanger materials, under conditions effecting selective adsorption of the plasma component on the chromatography membrane, and eluting tbe plasma component from the chromatography membrane,
        ii) applying eluate from the anion-exchange membrane chromatography to a chromatography membrane having immobilized thereon a ligand having particular affinity for the plasma component to effect adsorption of the plasma component on the chromatography membrane,
        iii) stepwise elution from the affinity-chromatography membrane by applying a solvent system employing
            a gradient of increasing ionic strength;
            different polarities, or
            different pH values
        to isolate the plasma component in a solvent-containing fraction;
    or
    d) removing solvent from the fraction to concentrate the plasma component, therein; and
    e) effecting virus-inactivation by treating
        i) the eluate from the solid-phase chromatography, prior to applying the eluate to a chromatography membrane, or
        ii) the fraction containing the plasma component, obtained by the stepwise elution from the chromatography membrane,
    with detergents in the presence of di- or trialkyl phosphate compounds.

2. The process of claim 1, wherein effluent of step a) is supplied to further work-up procedures for the recovery of other materials.

3. The process of claim 1, wherein adjustment of the ionic strength and/or of the pH value of the eluate to the condition of the following step takes place after step b).

4. The process of claim 1, wherein a membrane affinity chromatography is performed after step d).

5. The process of claim 1, wherein the eluate is collected that contains the products which have not already been removed, and optianally the further fractionation thereof by repeating membrane affinity chromatography wherein appropriate materials are used.

6. The process of claim 1, wherein a heat treatment is performed for virus inactivation.

7. The process according to claim 1, wherein the source containing the plasma component is blood plasma in fresh or thawed condition.

8. The process according to claim 1, wherein the solid phase extraction is effected by means of a cross-linked polysaccharide modified with basic groups or by means of anion exchanger membranes appropriately modified.

9. A process according to claim 1, wherein the membrane chromatography is carried out by using membranes which have been modified with DEAE or quaternary amines, or by using membranes which have been modified by low or high molecular weight affinity ligands capable of specifically binding to the desired plasma components (membrane affinity chromatography).

10. The process according to claim 1, wherein the affinity membrane chromatography is heparin affinity membrane chromatography, membrane immunoaffinity chromatography with immobilized antibodies against the substance to be isolated, or membrane affinity chromatography using membranes modified with hydrophobic ligands.

11. The process according to claim 10, wherein the hydrophobic ligands for modifying the chromatographic carrier are 2-hydroxyaminoalkyl groups such as 2-hydroxyaminopropyl and/or hydrophobic ligands such as propyl, butyl, phenyl groups and other similar ligands exhibiting some gradual change in hydrophobicity.

12. The process according to claim 1, wherein the adjustment of the ionic strength after the chromatographic steps is effected by dilution or desalting procedures such as dia- or ultrafilration or by the addition of agents increasing the ionic strength.

13. The process according to claim 1, wherein the virus-inactivation is effected by heating the fraction at from 55° C. to 70° C. for a period from 5 to 30 hours in the presence of stabilizers such as sugar, amino acids, bivalent cations and/or heparin.

14. The process according to claim 13, wherein the stabilizers are removed by desalting procedures such as diafiltration or ultrafiltration, by heparin affinity chromatography or anion exchanger chromatography or on carriers modified with DEAE or quatemary ammonium compounds or carriers modified with hydrophobic ligands.

15. The process according to claim 1, wherein the chromatography material is a particular material embedded in membranes and/or compact disks made of the respective materials.

16. The process according to claim 1, wherein the fractions obtained are concentrated by lyophilization or spray drying.

17. Process according to claim 1, wherein the anion exchanger group have been bonded to the fiber of the substrate material through spacers such as glucosamine moieties to form so-called tentacle material.

* * * * *